(12) United States Patent
Clark

(10) Patent No.: US 9,414,895 B2
(45) Date of Patent: *Aug. 16, 2016

(54) DENTAL MATRIX DEVICES SPECIFIC TO ANTERIOR TEETH, AND INJECTION MOLDED FILLING TECHNIQUES AND DEVICES

(76) Inventor: David J. Clark, Lakewood, WA (US)

(*) Notice: Subject to any disclaimer, the term of this patent is extended or adjusted under 35 U.S.C. 154(b) by 294 days.

This patent is subject to a terminal disclaimer.

(21) Appl. No.: 12/362,280

(22) Filed: Jan. 29, 2009

(65) Prior Publication Data

US 2009/0191505 A1    Jul. 30, 2009

Related U.S. Application Data

(60) Provisional application No. 61/024,473, filed on Jan. 29, 2008, provisional application No. 61/043,307, filed on Apr. 8, 2008.

(51) Int. Cl.
*A61C 5/04* (2006.01)
*A61C 5/06* (2006.01)

(52) U.S. Cl.
CPC . *A61C 5/062* (2013.01); *A61C 5/04* (2013.01); *A61C 5/045* (2013.01)

(58) Field of Classification Search
CPC .............. A61C 5/00; A61C 5/04; A61C 5/06; A61C 5/062; A61C 5/064; A61C 5/066; A61C 5/068; A61C 5/125; A61C 5/127
USPC ............................................ 433/39, 155, 226
See application file for complete search history.

(56) References Cited

U.S. PATENT DOCUMENTS

| | | |
|---|---|---|
| 2,611,182 A | 9/1952 | Tofflemire |
| 3,108,377 A | 10/1963 | Meyer |
| 3,842,505 A | 10/1974 | Eames |
| 4,024,643 A | 5/1977 | Eisenberg |
| 4,259,070 A | 3/1981 | Soelberg et al. |
| 4,330,280 A | 5/1982 | Dougherty et al. |
| 4,337,041 A | 6/1982 | Harsany |
| 4,391,590 A | 7/1983 | Dougherty et al. |
| 4,468,199 A | 8/1984 | Weikel |
| 4,523,909 A | 6/1985 | Lazarus |
| 4,536,155 A | 8/1985 | Ireland |
| 4,553,937 A | 11/1985 | Ropers |
| 4,601,662 A | 7/1986 | Galler |
| 4,704,087 A | 11/1987 | Dragan |
| 4,718,849 A | 1/1988 | Von Weissenfluh et al. |
| 4,781,583 A | 11/1988 | Lazarus |
| 4,997,367 A | 3/1991 | Kassel |
| 5,017,140 A | 5/1991 | Ascher |
| 5,035,615 A | 7/1991 | Din |
| 5,104,317 A | 4/1992 | Riazi |
| 5,114,341 A | 5/1992 | Kassel |

(Continued)

OTHER PUBLICATIONS

Ferracone, "Current Trends in Dental Composites", Crit Rev Oral Biol Med, 6(4), pp. 302-318, 1995.

(Continued)

*Primary Examiner* — Yogesh Patel
(74) *Attorney, Agent, or Firm* — Quarles & Brady LLP

(57) ABSTRACT

The present invention relates to methods for the restoration of a decayed portion of an anterior tooth or re-restoration of a previously filled anterior tooth, and to dental matrices and composite resin dispensers that may be used in the methods for the restoration of a decayed portion of an anterior tooth.

9 Claims, 10 Drawing Sheets

(56) References Cited

U.S. PATENT DOCUMENTS

| | | | |
|---|---|---|---|
| 5,425,635 A | 6/1995 | Croll | |
| 5,444,104 A * | 8/1995 | Waknine | 522/24 |
| 5,460,525 A | 10/1995 | Rashid | |
| 5,501,595 A | 3/1996 | Brorson | |
| 5,527,181 A | 6/1996 | Rawls et al. | |
| 5,607,302 A | 3/1997 | Garrison et al. | |
| 5,622,496 A | 4/1997 | Champagne | |
| 5,626,476 A | 5/1997 | Champagne | |
| 5,707,234 A | 1/1998 | Bender | |
| 5,730,592 A | 3/1998 | Meyer | |
| 5,807,101 A | 9/1998 | Scalzo | |
| 5,975,906 A * | 11/1999 | Knutson | A61C 5/125 128/DIG. 14 |
| 5,997,302 A | 12/1999 | Alpert | |
| 6,079,978 A | 6/2000 | Kunkel | |
| 6,142,778 A | 11/2000 | Summer | |
| 6,155,823 A | 12/2000 | Nagel | |
| 6,162,055 A | 12/2000 | Montgomery et al. | |
| D439,667 S | 3/2001 | Brown | |
| 6,206,697 B1 | 3/2001 | Hugo | |
| 6,232,367 B1 | 5/2001 | Kobashigawa et al. | |
| 6,234,793 B1 | 5/2001 | Brattesani et al. | |
| 6,236,020 B1 | 5/2001 | Friedman | |
| 6,261,094 B1 | 7/2001 | Dragan | |
| 6,312,254 B1 | 11/2001 | Friedman | |
| 6,315,566 B1 | 11/2001 | Shen et al. | |
| 6,319,002 B1 | 11/2001 | Pond | |
| 6,320,162 B1 | 11/2001 | Friedman | |
| 6,325,625 B1 | 12/2001 | Meyer | |
| 6,350,122 B1 | 2/2002 | Meyer | |
| 6,379,152 B1 | 4/2002 | Dragan | |
| 6,425,760 B1 | 7/2002 | Summer et al. | |
| 6,435,874 B1 | 8/2002 | Hughes | |
| 6,479,592 B2 | 11/2002 | Rheinberger et al. | |
| 6,482,007 B2 | 11/2002 | Stanwich et al. | |
| 6,540,072 B1 | 4/2003 | Fischer | |
| 6,593,395 B2 | 7/2003 | Angeletakis et al. | |
| 6,599,125 B1 | 7/2003 | Freilich et al. | |
| 6,616,448 B2 * | 9/2003 | Friedman | 433/32 |
| 6,619,956 B1 | 9/2003 | Weir | |
| 6,712,608 B2 | 3/2004 | Bills | |
| 6,756,417 B2 * | 6/2004 | Allred et al. | 522/13 |
| 6,761,562 B2 | 7/2004 | Von Weissenfluh | |
| 6,767,955 B2 | 7/2004 | Jia | |
| 6,787,629 B2 | 9/2004 | Jia et al. | |
| 6,890,176 B2 | 5/2005 | Hahn | |
| 6,893,258 B1 | 5/2005 | Kert | |
| 6,976,841 B1 | 12/2005 | Osterwalder | |
| 6,981,618 B2 * | 1/2006 | Reisinger | 222/326 |
| 7,001,932 B2 | 2/2006 | Blackwell et al. | |
| 7,014,462 B1 | 3/2006 | Tilse | |
| 7,097,364 B2 | 8/2006 | Wang | |
| 7,097,452 B2 | 8/2006 | Friedman | |
| 2001/0009755 A1 | 7/2001 | Fischer | |
| 2002/0115042 A1 * | 8/2002 | Hasel | 433/228.1 |
| 2002/0119424 A1 | 8/2002 | Margeas et al. | |
| 2002/0128347 A1 | 9/2002 | Blackwell et al. | |
| 2002/0172920 A1 * | 11/2002 | Bills | A61C 5/125 433/39 |
| 2003/0059741 A1 | 3/2003 | Bills | |
| 2003/0069326 A1 | 4/2003 | Stangel et al. | |
| 2003/0165793 A1 * | 9/2003 | Yobel et al. | 433/90 |
| 2004/0053189 A1 | 3/2004 | Friedman | |
| 2004/0229186 A1 | 11/2004 | Slone | |
| 2004/0234921 A1 | 11/2004 | Friedman | |
| 2005/0074716 A1 | 4/2005 | Cleary et al. | |
| 2005/0089814 A1 | 4/2005 | Slone | |
| 2005/0231983 A1 | 10/2005 | Dahm | |
| 2005/0255428 A1 * | 11/2005 | Coopersmith | A61C 5/125 433/222.1 |
| 2005/0256223 A1 | 11/2005 | Kolb et al. | |
| 2005/0287490 A1 | 12/2005 | Stookey et al. | |
| 2005/0287491 A1 | 12/2005 | Slone | |
| 2006/0009540 A1 | 1/2006 | Jia et al. | |
| 2006/0019217 A1 | 1/2006 | Yates | |
| 2006/0084029 A1 | 4/2006 | Viscomi et al. | |
| 2006/0088798 A1 | 4/2006 | Feinbloom et al. | |
| 2006/0110700 A1 | 5/2006 | Cipolla et al. | |
| 2006/0154197 A1 | 7/2006 | Gargiulo | |
| 2006/0155171 A1 | 7/2006 | Yang | |
| 2006/0188835 A1 | 8/2006 | Nagel et al. | |
| 2006/0275732 A1 | 12/2006 | Cao | |
| 2006/0275733 A1 | 12/2006 | Cao | |
| 2007/0099156 A1 * | 5/2007 | Wagner et al. | 433/228.1 |
| 2007/0148613 A1 | 6/2007 | Stoll | |
| 2008/0064012 A1 * | 3/2008 | Clark | A61C 5/125 433/226 |
| 2009/0208896 A1 * | 8/2009 | Clark | A61C 5/04 433/39 |

OTHER PUBLICATIONS

Mount et al., "Classification and Cavity Preparation for Caries Lesions", Jan. 2005, pp. 243-249.

Bayne et al., "A Characterization of First-Generation Flowable Composites", Journal of the American Dental Association, vol. 129, May 1998, pp. 567-577.

Braga et al., "Contraction stress of flowable composite materials and their efficacy as stress-relieving layers", Journal of the American Dental Association, vol. 134, Jun. 2003, pp. 721-728.

David J. Clark et al., "Optimizing Gingival Esthetics: A Microscopic Perspective", Oral Health, Apr. 2005, pp. 116-126.

David J. Clark et al., "Definitive Diagnosis of Early Enamel and Dentinal Cracks Based on Microscopic Evaluation", Journal of Esthetic and Restorative Dentistry, vol. 15 , 2003, pp. SI7-SI17.

Nordbo et al., "Saucer-shaped cavity preparations for posterior approximal resin composite restorations: Observations up to 10 years", Quintessence International, vol. 29, Issue 1, 1998, pp. 5-11.

McComb et al., "Systematic Review of Conservative Operative Caries Management Strategies", Journal of Dental Education, vol. 65, No. 10, 2001, pp. 1154-1161.

Downer et al., "How long do routine dental restorations last? A systematic review", British Dental Journal, vol. 187, No. 8, 1999, pp. 432-439.

Sensi et al., "Effect of Placement Techniques on the Marginal Adaptation of Class V Composite Restorations", The Journal of Contemporary Dental Practice, vol. 6, No. 4, Nov. 15, 2005, pp. 1-7.

Article from Fivesgroup.com, entitled "Induction Heating Principle", 2 pages, copyrighted 2009.

* cited by examiner

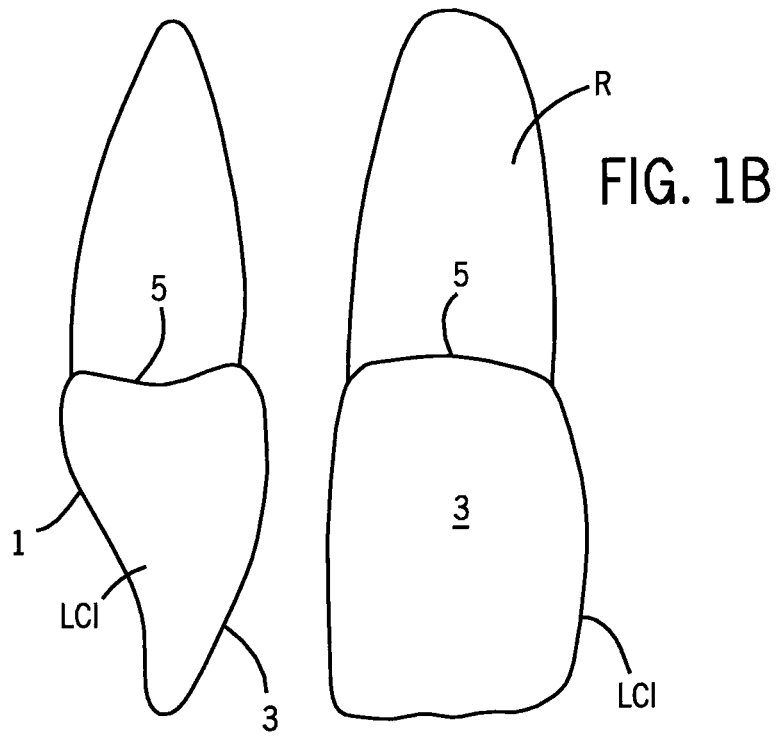
FIG. 1A
FIG. 1B
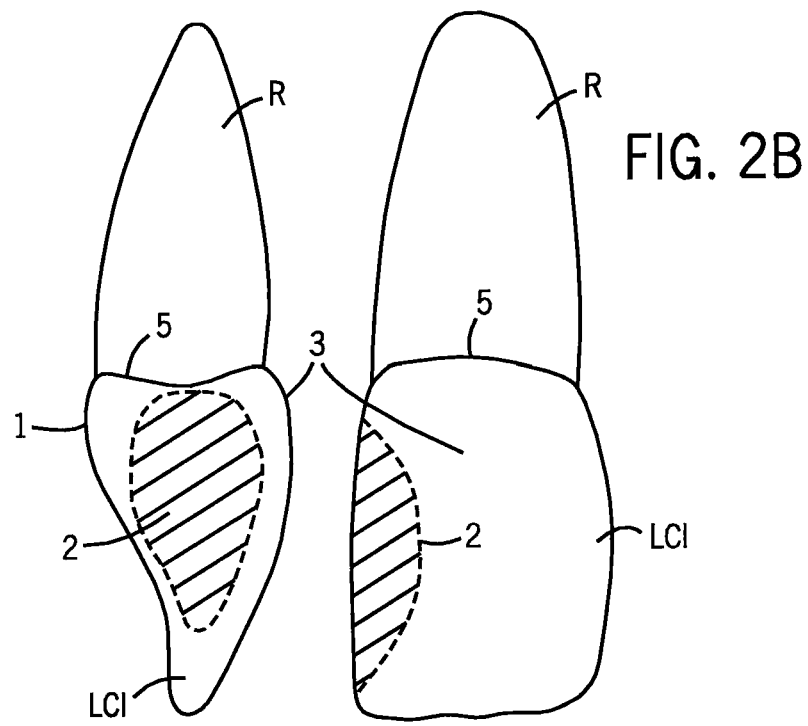
FIG. 2A
FIG. 2B

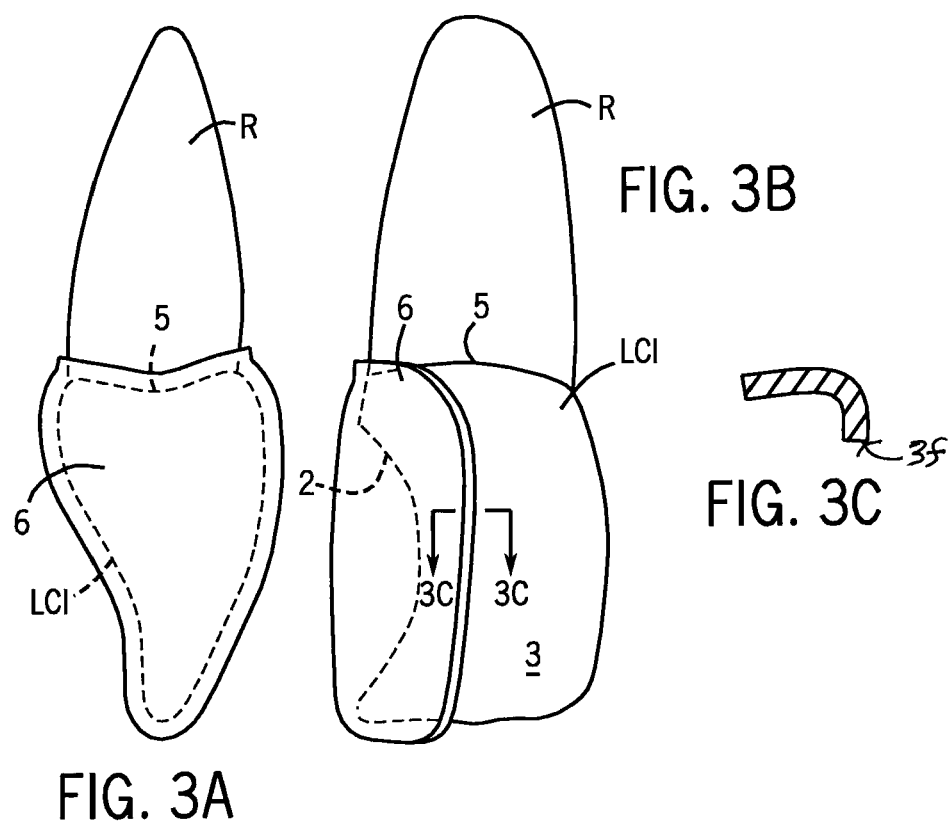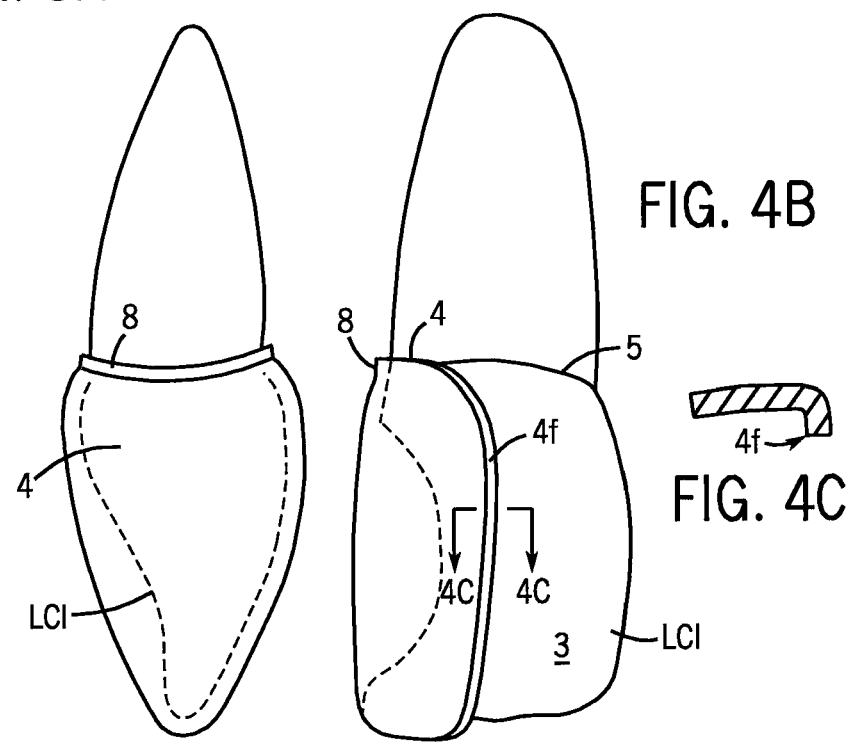

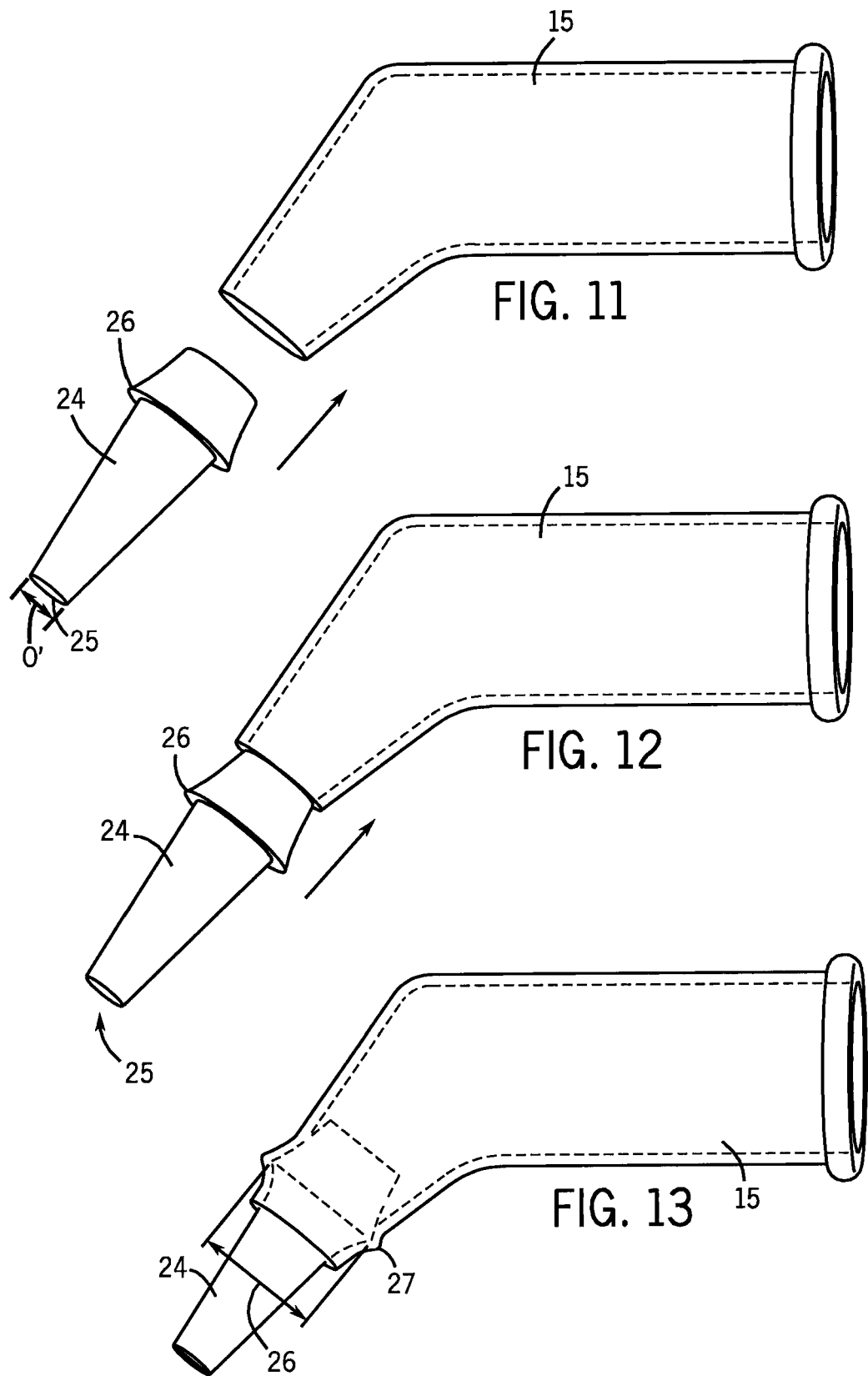

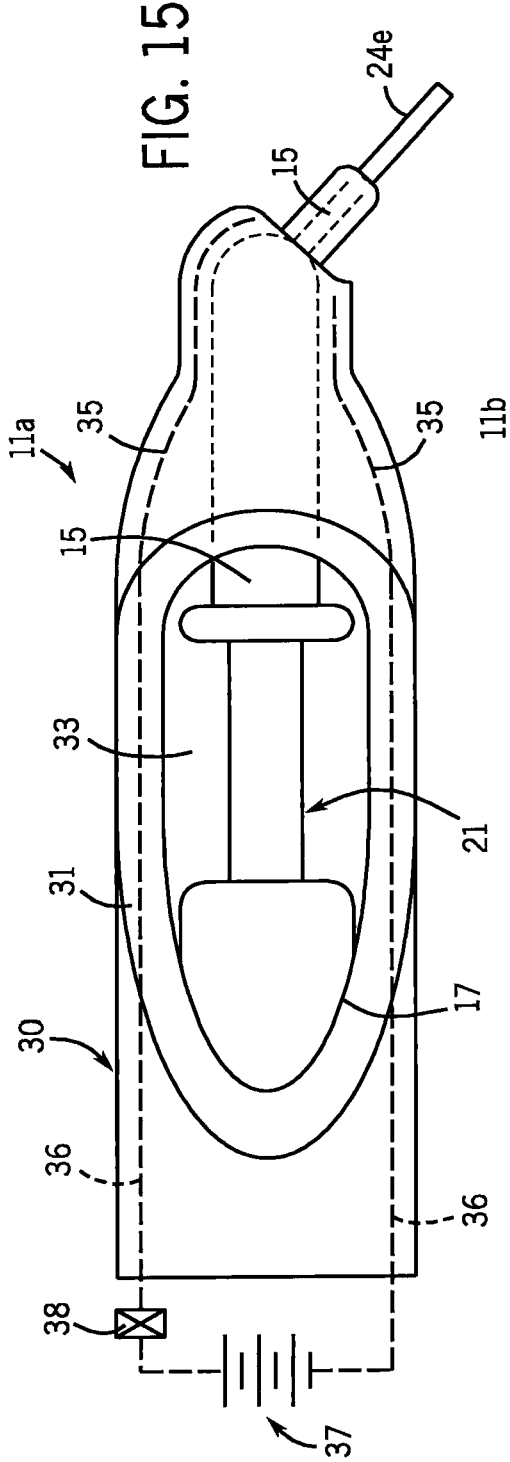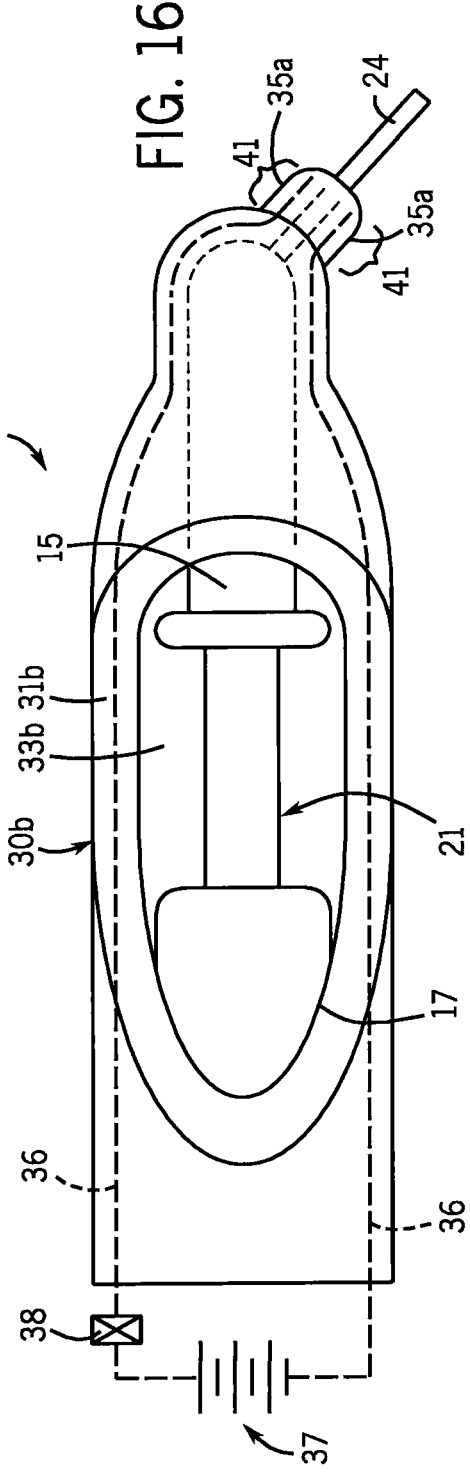

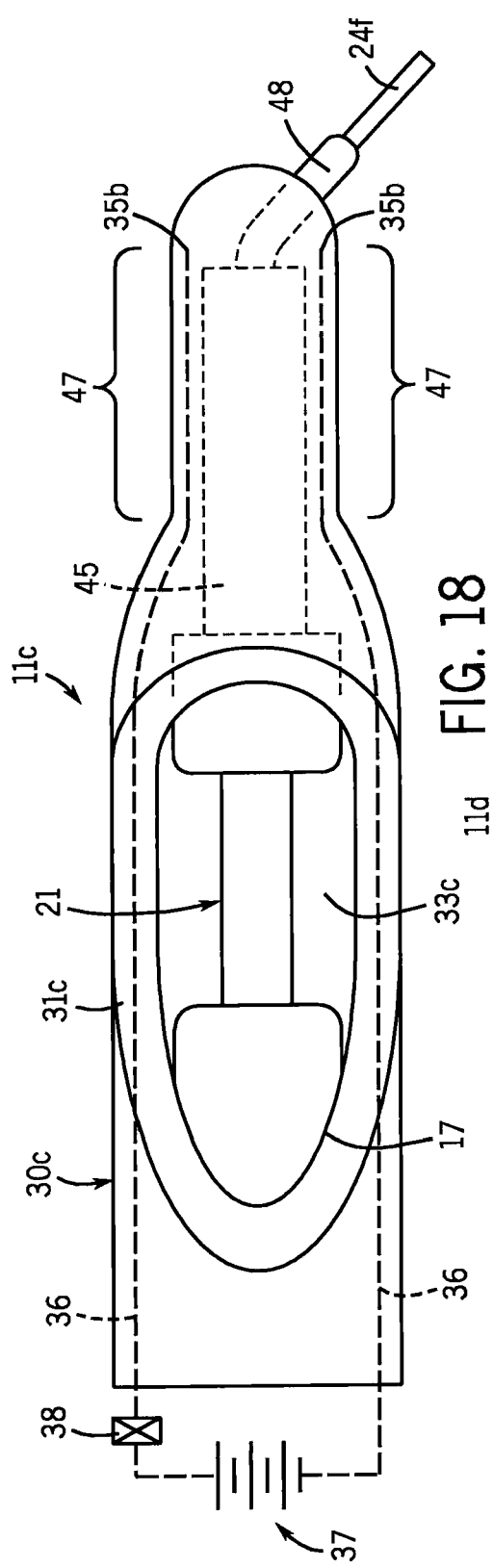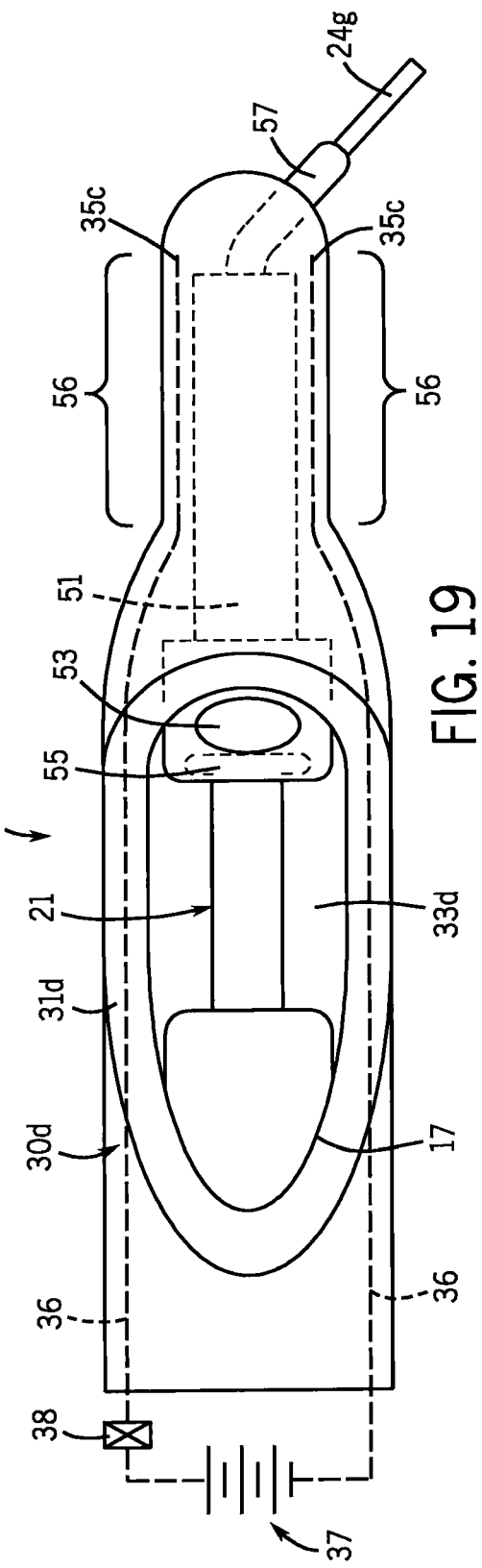

DENTAL MATRIX DEVICES SPECIFIC TO ANTERIOR TEETH, AND INJECTION MOLDED FILLING TECHNIQUES AND DEVICES

CROSS-REFERENCES TO RELATED APPLICATIONS

This application claims priority from U.S. Provisional Patent Application No. 61/024,473 filed Jan. 29, 2008 and from U.S. Provisional Patent Application No. 61/043,307 filed Apr. 8, 2008.

STATEMENT REGARDING FEDERALLY SPONSORED RESEARCH

Not Applicable.

BACKGROUND OF THE INVENTION

1. Field of the Invention

The present invention relates to methods for the restoration of a decayed portion of an anterior tooth or re-restoration of a previously filled anterior tooth, and to dental matrices and composite resin dispensers that may be used in the methods for the restoration of a decayed portion of an anterior tooth.

2. Description of the Related Art

Dental cavities that have spread to the dentin or have undergone cavitation are typically treated by removing the decayed portion of the tooth and thereafter filling the missing tooth structure with a restorative material such as silver (amalgam), white (resin), porcelain, or gold. Cavities that are located adjacent to neighboring teeth are called interproximal cavities.

When treating interproximal cavities, the dentist first removes the decayed portion of the side of the tooth. In order to properly deposit the restorative material on the side of the tooth without undesired leaking of the restorative material beyond the side of the tooth, the dentist places a dental matrix around at least a portion of the tooth. The dental matrix may be a metallic or plastic strip, and when the matrix is placed around at least a portion of the tooth, the matrix acts as a form for the desired shape of the restored tooth. Various dental matrix bands are shown in U.S. Pat. Nos. 6,712,608, 6,619, 956, 6,350,122, 6,142,778, 6,079,978, 5,975,906, 5,807,101, 5,730,592, 5,622,496, 5,501,595, 5,460,525, 5,425,635, 5,114,341, 4,997,367, 4,781,583, 4,718,849, 4,704,087, 4,601,662, 4,553,937, 4,536,155, 4,523,909, 4,024,643, 3,842,505, 3,108,377, and 2,611,182, and U.S. Patent Application Publication Nos. 2006/0019217 and 2005/0089814. The disadvantages of these known matrix bands is that they are not truly anatomic and therefore, they must be conformed to the tooth by pressure or other means. As a result, these matrixes are inefficient in that more dentist time is needed to complete the restoration, and the final result may be a non-anatomic restoration.

In the past a flat clear (e.g., Mylar™ plastic) strip was placed after the cavity was prepared and often adapted with an interdental wedge or elastic spacer. There have been problems with previous techniques. The problems with traditional clear Mylar™ plastic strips are that they are flat and require wedging, and do not conform to the tooth.

After the cavity was prepared, the composite was placed onto or partially injected onto the tooth. The composite was then packed into the cavity preparation. Finally, the flat clear or metallic matrix was engaged with fingers or instruments to wrap around the tooth, and then simultaneously a light cure unit was placed in proximity to the tooth to initiate photo-curing or polymerization of the composite. Holding all four ends of the strips while simultaneously light-curing is always a challenge. The problems of the traditional technique included flat interdental shapes that are an esthetic and health liability. In particular, the "dark triangle" that often occurs is caused by insufficient buttressing of the gingival triangle which is seeking two approximating rounded interdental tooth profiles.

It is believed that no attempt has been made to present for a sectional curved and or anatomically shaped nor tooth specific matrix nor surface specific matrix for anterior teeth.

The anterior tooth has a complex shapes with multiple curvatures. It is asymmetrical from front side to back side (facial to lingual) and from right to left (mesial to distal). Sectional clear flat matrix strips for anterior teeth have been available. These fillings today are performed nearly universally with tooth colored filling materials (composite resin) and require a medium to contain the filling material inside the cavity preparation. These matrix strips are translucent, and typically made from Mylar™ plastic material that is thin and pliable. It is believed that to date there are no sectional matrices available for anterior teeth other than a flat Mylar™ plastic strip.

It is believed that the only anatomic (non-flat) shaping device for anterior teeth currently sold is a strip crown that is formed from a stiff material such as polycarbonate. They are used for temporization or building up of a severely broken down tooth. Composite material is placed inside of the strip crown, cured with light or chemical polymerization, and then the polycarbonate can be stripped away (in the case of a long term "build-up", such as is done until permanent dentistry is undertaken) leaving a tooth built up with composite. The relatively crude shape of the buildup is then eventually prepared (ground down) to the peg shape typically performed in preparation for a veneer-crown. A crown is then fabricated in a laboratory or with CAD CAM and then the tooth receives a crown to permanently cover the "build-up". Alternatively the strip crown can be left in place as a temporary veneer crown. The thickness and stiffness of the "strip crown" disallows its use for interproximal fillings. Hence the use of flat Mylar™ plastic strips is the norm today.

Some problems with current flat plastic matrix strips for anterior teeth include: (1) the flat plastic matrix strips are flat (not anatomic), requiring crimping; (2) the flat plastic matrix strips require stabilizing with wedges or other devices; (3) the flat plastic matrix strips require further stabilizing with the operator's fingers or the dental assistant's fingers, and back to back fillings (two neighboring teeth with interproximal caries or failing fillings) present extreme challenges to manipulate four matrix ends simultaneously; (4) the flat plastic matrix strips require that the strip be "wrapped" to approximate the tooth after placement of filling material (such as a composite, glass ionomer, composite/glass ionomer mix) and prior to polymerization or light curing of the material; (5) time and energy is usually expended to remove excess and areas of bulky, non anatomic regions of the composite filling material because of the residual contour created by the flat, non anatomic clear strip; (6) the above mentioned finishing can lead to gum trauma and can lead to iatrogenic gouging of tooth surface and tooth surfaces of neighboring teeth; (7) the above mentioned finishing disturbs the smooth and highly cured surface left by the plastic strip and while this disturbed surface can be polished, it is virtually impossible to return to the original smoothness and these surfaces are manifested clinically as a matte finish, rough finish, or jagged finish and these three imperfect finish types collect bacteria more readily, are more prone to discoloration and predispose the tooth to decay and predispose the periodontal attachment (gum and bone) to deterioration from the destructive nature of periodontal diseases; (8) the flat matrix strip combined with a wedge often results in a flat contoured filling that has an unsightly gapping (dark triangle) between the teeth at the gum attachment area such that food and bacterial accumulation are also more common in these gaps; and (9) the pre curved sectional matrix bands for posterior teeth are too short to be used easily on anterior teeth as matrix bands for posterior teeth range from 4.5 millimeters to 6.5 millimeters in height, and the needs of anterior teeth range approximately from 8 millimeters to 13 millimeters in height.

Thus, there is a need for improved dental matrices, particularly dental matrices intended for anterior teeth.

As detailed above, removed tooth structure is often filled with a composite restorative material such as white filled resin. While flowable composites have been available for quite some time and can provide for ease of filling intricate dental cavity preparations, the ability of paste composite material to flow and adapt to the intricacies of a dental cavity preparation can be compromised if the viscosity of the paste composite is too high. Thus, paste composite can pose difficulties in advanced injection molded cavity preparation and filling techniques such as that described in U.S. Patent Application Publication No. 2008/0064012. However, in comparison to flowable composite, paste composite has been shown to be superior in that paste composite has less polymerization shrinkage, less wearing over years of mastication, improved polishability, and improved strength.

It has been proposed that dental materials can be heated before or during extrusion to reduce viscosity so that the restorative material expressed from a dental capsule can better adapt to the walls of a cavity preparation and to the intricacies of the cavity preparation. See, for example, U.S. Pat. Nos. 6,312,254, 6,320,162, 6,616,448 and 7,097,452. Although some benefits of heated composite materials have been reported in these patents, adoption of this technique has been very limited. Composite manufacturers have not adopted significant changes to their delivery systems to capitalize on the concept and benefits of heated composite. For example, the tip orifice size of typical current paste composite syringes (examples include Filtek Supreme PLUS™ available from 3M, St. Paul, Minn., USA) is significantly larger than the orifice tip size of the flowable type composites. In the case of this example product from 3M, the paste syringe orifice is approximately 2.5 millimeters in diameter, while the 3M flowable composite tip size is less than 1 millimeter. See also, U.S. Pat. No. 7,001,932 in which a composite is filled in a syringe having an internal tip diameter of 2 millimeters.

Accordingly, it can be appreciated that in the field of composite dental restorative materials, there is a need for improved composite dispensers and methods such that paste composite can have its handling characteristics improved to handle more like the less robust but easier to apply flowable composites.

SUMMARY OF THE INVENTION

The invention meets the foregoing needs by providing improved methods, dental matrices, composite dispensers, and kits for the restoration of a decayed portion of an anterior tooth.

In one aspect of the invention, there is provided a dental matrix including a non-flat sectional strip dimensioned for anterior teeth. The matrix can be anatomic. The matrix can be translucent. The matrix can be pre-curved and universal for any interproximal surface of any anterior tooth. The matrix can include one or more anatomic features. The matrix can include a pronounced root-crown interface. In one form, the matrix is side specific. The matrix can be labeled as upper anterior tooth-right side, upper anterior tooth left side, lower anterior tooth right side or lower anterior tooth left side. The matrix can be tooth specific (e.g., maxillary right central incisor). The matrix can be tooth and surface specific (e.g., upper right central incisor, mesial surface). The matrix can be fully anatomic (as opposed to simply pre-curved or having one or more anatomic features). The matrix can be anatomically shaped such that the matrix is self stabilizing and hands free. The matrix can include a side flange that extends away from the tooth.

In another aspect, the invention provides a dental matrix including a non-flat sectional strip having a first end and an opposed second end. The strip includes at least one anatomic feature, and the strip has a length from the first end to the second end such that the strip can cover from 90 degrees up to 359 degrees around a side surface of a tooth covered by the strip. The strip can have a length from the first end to the second end such that the strip can cover from 90 degrees up to 270 degrees around the side surface of the tooth covered by the strip. The strip can have a length from the first end to the second end such that the strip can cover from 90 degrees up to 180 degrees around the side surface of the tooth covered by the strip. The strip can have a length from the first end to the second end such that the strip can cover from 90 degrees up to 120 degrees around the side surface of the tooth covered by the strip. The strip can be dimensioned for anterior teeth. The matrix can be translucent. The matrix can be pre-curved and universal for any interproximal surface of any anterior tooth. The matrix can be tooth specific. The matrix can be tooth and surface specific. The matrix can be fully anatomic.

In yet another aspect, the invention provides a dental matrix including a non-flat sectional strip having a first end and an opposed second end. The strip includes at least one anatomic feature, and the strip has a length from the first end to the second end such that the strip can cover 360 degrees around a side surface of a tooth covered by the strip. The strip can have a length from the first end to the second end such that the strip can cover from 360 degrees up to 420 degrees around the side surface of the tooth covered by the strip. The matrix can be translucent. The matrix can be pre-curved and universal for any interproximal surface of any anterior tooth. The matrix can be tooth specific. The matrix can be tooth and surface specific. The matrix can be fully anatomic.

In still another aspect, the invention provides an injection molded tooth restoration method that can only be accomplished with a relatively precise fit of any of the preceding matrices according to the invention to the tooth being restored.

In yet another aspect, the invention provides a method for the restoration of a tooth having an original shape including an interproximal surface. The method includes: (a) removing a portion of the interproximal surface of the tooth to form a hollow cavity preparation; (b) surrounding the removed portion of the interproximal surface of the tooth with any of the preceding matrices according to the invention; (c) placing a light-curable resin tooth bonding agent into the cavity preparation; (d) extruding a heated light-curable paste composite resin into the pool of the flowable composite before light curing the pool of the flowable composite; and (e) simultaneously light curing the bonding agent and the paste composite resin contained in the cavity preparation. Step (d) can comprise extruding the paste composite resin through a step down tip. Step (d) can comprise extruding the paste composite resin through a step down tip inserted into a composite capsule. Step (d) can comprise extruding the paste composite resin through a step down tip inserted into a composite capsule wherein the tip has a rib to resist dislodgement from the capsule.

In still another aspect, the invention provides a dental composite dispenser including a housing including an end section for dispensing composite; an electrical power supply; at least one resistive heating element in electrical communication with the power supply where each heating element is located in the end section of the housing; and a source of composite in the end section of the housing. The source of composite includes a removable hollow step down tip through which heated composite flows out of the source of composite. In one form, the step down tip has an inside diameter in the range of about 0.4 millimeters to about 1.6 millimeters. The source of composite can be a capsule or a syringe, or a chamber in the end section of the housing. In one form, the source of composite is a capsule, and each heating element is located only near the tip of the capsule. In another form, the source of composite is a syringe, and the housing includes a plunger sized to express composite from the syringe. In another form, the electrical power supply includes an AC power cord. In another form, the electrical power supply includes a battery.

In still another aspect, the invention provides a method for dispensing composite from a dental composite dispenser. The method includes: loading a source of composite in the end section of the dispenser; inserting a hollow step down dispensing tip in the source of composite; and extruding composite out of the tip. The source of composite can be heated before extruding composite out of the tip. The step down tip can have an inside diameter in the range of about 0.4 millimeters to about 1.6 millimeters.

Thus, this aspect of the invention includes the manufacture of removable dispensing tips that have tip sizes and shapes specific to the extrusion of paste composite dental filling material that has been pre-warmed or directly altered during extrusion, the alteration of the physical characteristics of the composite from heat and/or extreme pressure; or other means of altering the physical properties to allow increased flowability of the paste composite. These tips can be (i) fastened to the composite heating extrusion gun, (ii) warmed and/or fastened to pre-warmed syringes, or (iii) fastened to traditional hand held dispensing guns; which then together have been pre-warmed in a warming device. The small removable tips with a reduced tip orifice size allow for: (i) the direct placement into cavities that are smaller than the circumference of traditional paste capsule tip orifice size, (ii) an injection molded composite technique which requires deeper insertion of the capsule tip into the cavity preparation, and (3) use with anatomic and pre-curved matrices that impede the insertion of larger, traditional tip orifices. The invention satisfies a need for a system that includes small removable dispensing tips for extruding paste composite through an orifice size that requires a physical change of the paste, including but not limited to heat and high pressure. Many of the paste composites experience a phenomenon of being thixotropic, i.e., the paste temporarily flows better with reduced viscosity. Thus, a capsule with removable tips of small orifice size for paste composite has many advantages.

In yet another aspect, the invention provides a dispenser for supplying a dental restorative material to a cavity preparation. The dispenser includes a hollow body having an inner surface and a proximal opening at a proximal end of the body. The dispenser includes a movable piston engaging the inner surface of the body where the piston seals the proximal opening of the body. The piston and the inner surface define an interior space of the body. The dispenser includes a hollow dispensing orifice having a passageway extending from an inlet to an outlet where the inlet is in fluid communication with the interior space of the body. The dispenser includes a dental restorative material in the interior space of the body where the dental restorative material is a paste composite including a resin and a filler. Movement of the piston toward the dispensing orifice extrudes dental restorative material from the outlet of the dispensing orifice. The passageway of the dispensing orifice can have an inside diameter in the range of about 0.4 millimeters to about 1.8 millimeters.

This aspect of the invention is a preloaded body (e.g., a capsule) that is designed to be used in conjunction with heated extrusion, or extruded with forces that are greater than currently produced with current hand lever type dispenser systems. In other words, this aspect of the invention is any packaging of paste composite into a delivery system body (e.g., unidose capsules, syringes with removable or fixed tips, tubs, tips, mixing tips (i.e., for A-B chemical cure, or dual cure with A-B chemical cure plus light cure) where the dispensing orifice size requires heat or extreme pressure to allow it to work.

Thus, this aspect of the invention includes the manufacture and placement of paste composite dental filling material into preloaded unidose type capsules; capsules which possess reduced tip orifice size through which the extrusion of the paste composite through the smaller dispensing orifice is dependent on alteration of the physical characteristics of the paste composite from heat and/or extreme pressure or other means by which the physical properties of the paste composite are altered to allow increased flowability (such as vibration, ultrasonic energy, microwaves, or similar physical and thermal energies). The small dispensing orifice with a reduced tip orifice size allows for: (i) the direct placement into cavities that are smaller than the circumference of traditional paste capsule tip orifice size, (ii) an injection molded composite technique which requires deeper insertion of the capsule tip into the cavity preparation, and (3) use with anatomic and pre-curved matrices that impede the insertion of larger, traditional tip orifices.

This aspect of the invention further includes the manufacture of disposable capsules with a reduced tip dispensing orifice size, for subsequent loading of a pre-measured amount of paste composite dental filling material, the extrusion of which through the smaller dispensing orifice is dependent on alteration of the physical characteristics of the paste composite from heat and/or extreme pressure; or other means of altering the physical properties to allow increased flowability of the paste composite. The wall of the dispensing orifice can be thicker than the inside diameter of the passageway of the dispensing orifice to be of increased strength to withstand the increased pressure. This aspect of the invention satisfies the need for a preloaded paste composite capsule with a small dispensing orifice. That is because paste composites are too viscous to be extruded or injected through smaller orifices. The invention satisfies a need for a system that includes small dispensing orifices for extruding paste composite through an orifice size that requires a physical change of the paste, including but not limited to heat and high pressure. Many of the paste composites experience a phenomenon of being thixotropic, i.e., the paste temporarily flows better with reduced viscosity. A capsule according to the invention with a dispensing orifice with reduced tip orifice size for paste composite has the advantages of the above mentioned tips. Extreme pressure is defined as pressure beyond what is currently produced in the available dispensing guns with manual levers. Heat is defined as temperatures above room temperature, preferably from 70° F. to 180° F. This increased temperature can produced either in hot plates, or dedicated composite pre-warmers such as that shown in U.S. Patent Application Publication No. 2004/0234921, or in the direct heating as in versions of the present invention.

In still another aspect, the invention provides for the manufacture of a dental composite filling material with altered filler particle composition that utilizes (i) elevated filler particle content by weight and/or volume, or (ii) particle shape modification, or (iii) modification of particle configuration such as pre-sintering, or (iv) utilization of pre-cured heavily filled composites which are then ground and re-mixed with uncured composite with a more usable filler percentage, or (v) altered chemistry of the organic binding resin (e.g., a Bis-GMA or silorane), to achieve minimized polymerization shrinkage, less than 1% and approaching 0%, and the placement of the composite may only be possible if it were heated and/or extreme pressure, vibration, ultrasonic energy, microwaves, or similar physical and thermal energies were applied prior to placement to achieve this temporary reduction in viscosity and thixotropic (sheer thinning) affect.

It is one advantage of the invention to provide a composite dispenser in which paste composite can be treated to act like flowable composite when filling a cavity preparation. The composite dispenser allows paste composite to be used in injection molded cavity preparation and filling techniques with better handling and placement. The composite dispenser also allows paste composite to be used to fill smaller cavity preparations. In addition, the small orifice diameter of the composite dispenser applies shear stresses to the paste composite that lower the viscosity of the paste composite.

It is another advantage of the invention to provide a composite dispenser in which paste composite can be substituted for flowable composite when filling a cavity preparation. The use of paste composite overcomes the problems of flowable composite such as the increase shrinkage of flowable composites, the lower polishability of cured flowable composite, the lower wear resistance of cured flowable composite, and the lower strength of cured flowable composite.

It is yet another advantage of the invention to provide a method of filling a cavity preparation using an anatomic matrix and a composite dispenser in which paste composite can be substituted for flowable composite. Previous techniques for placement of the paste composite are not truly injection molded. Rather they are placed with a small spatula, layered and or packed. Prior matrices do not allow injection molding because they are not anatomically shaped and or the cavity shape does not support an injection molded technique. Additionally, the lack of translucency of the matrix demands incremental loading. Also, the tip sizes of the composite syringes are too large to insert deep enough into the cavity shapes. Injection molding can be accomplished by modifying the pressure applied during composite delivery, or modifying the temperature and/or thixotropic state of a paste composite to allow it to be injected without the use of lesser filled resins such as flowable resin.

It is still another advantage of the invention to provide a composite dispenser in which paste composite can be substituted for flowable composite when filling a cavity preparation. The paste composite can be super filled or otherwise modified such that it would be so heavy and thick that the dentists would have trouble placing it using conventional techniques. The paste composite is heated and extruded so that it acts like normal paste. For an injection molding technique, the paste composite will work readily, whereas with the old fashioned approach of spooning paste composite or packing paste composite into the tooth, the paste composite could begin to cool and thicken and become unusable before the dentist finished placing it. The heavy viscosity is a benefit in the injection molded technique.

The features, aspects, and advantages of the present invention will become better understood upon consideration of the following detailed description, drawings and appended claims.

BRIEF DESCRIPTION OF THE DRAWINGS

FIG. 1A is a right side view of a human left central incisor.

FIG. 1B is a front view of a human left central incisor.

FIG. 2A is a right side view similar to FIG. 1A showing an area of interproximal decay or of a previously placed filling.

FIG. 2B is a front view similar to FIG. 1B showing an area of interproximal decay or of a previously placed filling.

FIG. 3A is a right side view similar to FIG. 1A showing a side specific matrix on the left central incisor.

FIG. 3B is a front view similar to FIG. 1B showing a side specific matrix on the left central incisor.

FIG. 3C is a cross-sectional view taken along line 3C-3C of FIG. 3B.

FIG. 4A is a right side view similar to FIG. 1A showing a matrix on the left central incisor, the matrix being a universal sectional type matrix for anterior teeth with multiple anatomic features but not side or surface specific.

FIG. 4B is a front view similar to FIG. 1B showing a matrix on the left central incisor, the matrix being a universal sectional type matrix for anterior teeth with multiple anatomic features but not side or surface specific.

FIG. 4C is a cross-sectional view taken along line 4C-4C of FIG. 4B.

FIG. 11 shows a step-down tip before insertion in the end of the capsule of FIGS. 6-10.

FIG. 12 shows the step down tip being inserted in the capsule of FIGS. 6-10.

FIG. 13 shows the step down tip fully inserted into the capsule of FIGS. 6-10.

FIG. 15 shows a view taken along lines 15-15 of FIG. 7 showing one version of a composite dispenser having means for heating the capsule of FIGS. 6-10.

FIG. 16 is a view similar to FIG. 15 showing another version of a composite dispenser having means for heating the capsule of FIGS. 6-10.

FIG. 18 is a view similar to FIG. 15 showing another version of a composite dispenser having means for heating the syringe of FIG. 17.

FIG. 19 is a view similar to FIG. 15 showing another version of a composite dispenser having means for heating a chamber that is filed with composite resin.

Like reference numerals will be used to refer to like parts from Figure to Figure in the following description of the drawings.

DETAILED DESCRIPTION OF THE INVENTION

Figure 5A:
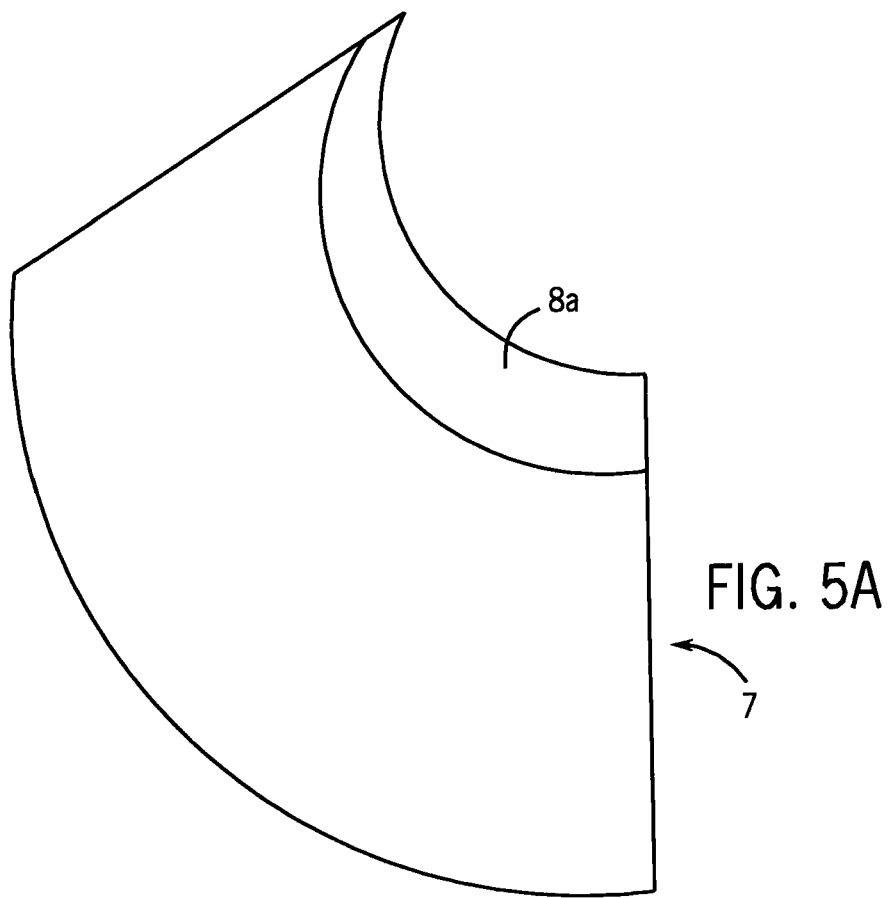
FIG. 5A is a perspective view of a pre-curved matrix specific to anterior teeth with one anatomic feature.

The invention provides improved methods, dental matrices, composite dispensers, and kits for the restoration of a decayed portion of an anterior tooth.

In an example method according to the invention for the restoration of a tooth, the dentist locates a tooth having a cavity. A hollow cavity preparation is prepared in a tooth. The tools and techniques for forming the hollow cavity preparation are well known in the art and therefore will not be explained further.

In order to properly deposit the restorative material on the side of the tooth without undesired leaking of the restorative material beyond the side of the tooth, the dentist places a dental matrix around at least a portion of the tooth. In the invention, a sectional anatomic translucent dental matrix is placed on the tooth. When the matrix is placed around at least a portion of the tooth, the matrix acts as a form for the desired shape of the restored tooth.

The cavity preparation in the tooth is then etched with liquid and/or gel phosphoric acid. The cavity preparation in the tooth is then rinsed and dried. A lightly filled or unfilled light curable resin tooth bonding agent is then applied to the tooth covering the entire cavity preparation. The resin tooth bonding agent is then air thinned except on the tooth surface where a small pool of resin tooth bonding agent is maintained. The resin tooth bonding agent is not light cured at this point. Resin tooth bonding agents improve composite to enamel and/or dentin bonding. One example resin tooth bonding agent is available under the tradename OptiBond Solo Plus®.

A light curable flowable composite resin is then injected directly into the pool of resin tooth bonding agent (under magnification if possible) without incorporating bubbles. A tiny amount of the light curable flowable composite resin is expressed before placement to ensure that there is no air in the cannula. The light curable flowable composite and resin tooth bonding agent are not light cured at this point. Generally, light curable flowable composite resins contain 20-25 percent less filler in the light curable polymeric material than nonflowable paste materials. Light curable flowable composite resins are available under tradenames such as Filtek™, Flow-It™, EsthetX®, Revolution®, AeliteFlo®, PermaFlo®, Dyract Flow®, Tetric®, and Heliomolar®. Light curable resins are preferred as light cured resins are more color stable than chemically cured resins.

A light curable paste composite resin is then extruded into the pool of flowable composite resin and resin tooth bonding agent without creating air bubbles, allowing the composite resin to displace most of the lesser filled flowable composite resin and resin tooth bonding agent (under magnification if possible). Composite resins are available under tradenames such as 3M Z100™, 3M Filtek Supreme™, and Prodigy®. The next steps are burnishing, carving the anatomy and carving excess composite. There is no need to use a condenser or plugger.

The filled cavity preparation is then cured using a curing light such as high intensity light emitting diode (LED) lights, plasma-arc curing lights, halogen lights, and laser lights. The matrix is then removed, and the restored tooth is polished with discs, strips, and rubber tipped and carbide burs.

Optionally, flowable composite resin is not used in the method. In this version of the method, heating the paste composite allows the more highly filled paste composite to be expressed through step down tips according to the invention having smaller inside diameters (about 0.4 millimeters to about 1.6 millimeters).

Looking at FIGS. 1A-5B, there is shown the lingual, (palatal or inside) surface 1 of a left central incisor (LCI), or anterior tooth. The cross hatched area 2 is an area of interproximal decay or of a previously placed filling. The facial (buccal or outside) surface 3 of tooth LCI is also shown. The cemento-enamel junction (crown-root interface) is shown at 5.

Various matrices are provided by the invention. Each matrix can be tooth specific, or the matrix can be tooth type specific, or the matrix can be tooth surface specific. By "tooth specific" it is meant that the matrix is configured to conform to the shape of the outer surface of the specific natural tooth being restored such as (without limitation) an upper left central incisor. By "tooth type specific" it is meant that the matrix is configured to conform to the shape of the outer surface of the specific type of natural tooth being restored such as (without limitation) an upper incisor. By "tooth surface specific" it is meant that the matrix is configured to conform to the shape of the outer surface of the specific natural tooth surface being restored such as (without limitation) an upper left incisor mesial surface.

In FIGS. 3A and 3B and 3C, a side specific matrix 6 for anterior teeth is shown. The matrix 6 has a side terminal flange 3f that extends away from the surface of the tooth LCI when the matrix 6 is placed on the tooth LCI. This example would be designated as right side or right hand specific. "Mesial and Distal" orientation is the common anatomic description but the side specific, "right hand" or "right side" naming signifies that the matrix can be used only on the right side of the tooth, which would be the distal surface of a right maxillary (upper) central incisor, or a right maxillary lateral incisor or a right maxillary canine tooth. Conversely the "right hand specific anterior matrix" would be used for the mesial surface of a maxillary left central incisor, or a maxillary left lateral incisor, or a maxillary left canine tooth. The mandibular (lower) anterior teeth would be the inverse orientation of the maxillary teeth. They are labeled as "right hand" or "left hand" specific to account for the asymmetrical shape of the tooth. In this variation, the cingulum shape of the lingual surface is representational and therefore the matrix is not universal and therefore the operator must choose the specific matrix and orientation for the matrix.

In FIGS. 4A and 4B, a universal sectional type matrix 4 for anterior teeth with multiple anatomic features but not side or surface specific features is shown. The matrix 4 has a root-crown interface 8 and a side terminal flange 4f that extends away from the surface of the tooth LCI when the matrix 4 is placed on the tooth LCI. The matrix 4 can be translucent, sectional, and/or anatomically shaped. The matrix 4 as shown is partially anatomic (i.e., it is less than all anatomic). However, a fully anatomic matrix is also in accordance with the invention. By "anatomic", it is meant that the matrix has an inner surface that conforms to the shape of the outer surface of the region of the natural tooth being restored.

The sectional matrix 4 can cover from 90 degrees up to 359 degrees around the lingual side surface 1 and the facial side surface 3 of the tooth LCI. Preferably, the sectional matrix 4 can cover from 90 degrees up to 270 degrees around the lingual side surface 1 and the facial side surface 3 of the tooth LCI. More preferably, the sectional matrix 4 can cover from 90 degrees up to 180 degrees around the lingual side surface 1 and the facial side surface 3 of the tooth LCI. Most preferably, the sectional matrix 4 can cover from 90 degrees up to 120 degrees around the lingual side surface 1 and the facial side surface 3 of the tooth LCI. Alternatively, a 360 degree partially anatomic or fully anatomic matrix that can either be continuous or with a cut can be provided. In another alternative, a 360 to 420 degree partially anatomic or fully anatomic matrix with a cut and purposeful overlap to accommodate different variations in circumference of teeth that is seen between different individuals can be provided.

Figure 5B:
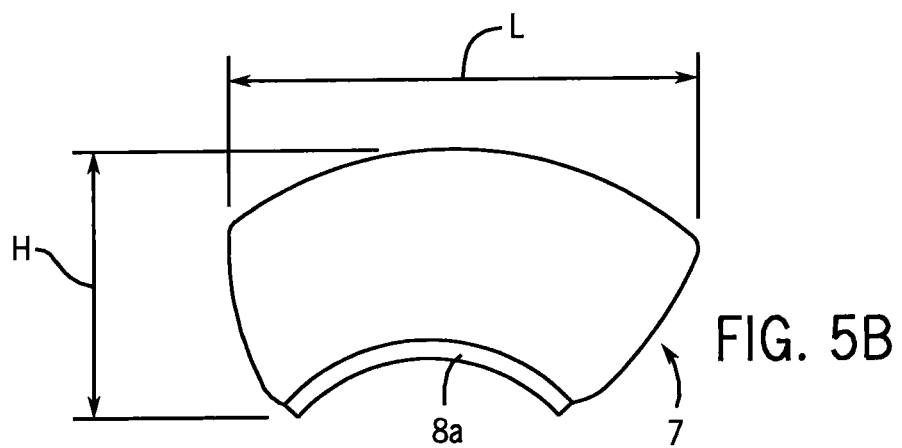
FIG. 5B is an inverted side view of the pre-curved matrix of FIG. 5A.

In FIGS. 5A and 5B, there is shown, a side view of a pre-curved matrix 7 specific to anterior teeth with one anatomic feature which is the root-crown interface 8a. In the example matrix 7 of FIGS. 5A and 5B, the length L of the pre-curved matrix 7 is approximately 13 millimeters and the height H can range approximately from 10 millimeters to 13 millimeters.

A matrix according to the invention can be anatomically shaped such that the matrix is hands free and self stabilizing (i.e., there is no requirement for a matrix stabilizer that conforms the matrix to the tooth). However, in a two step process, a dentist can forgo the use of a matrix stabilizer for the first step when the cavity is deep and or on the root surface and first apply flowable composite and/or paste composite to create an undercut that will allow the subsequent use of a matrix stabilizer with more ease in a single step injection molding technique to finish the filling.

Figure 6:
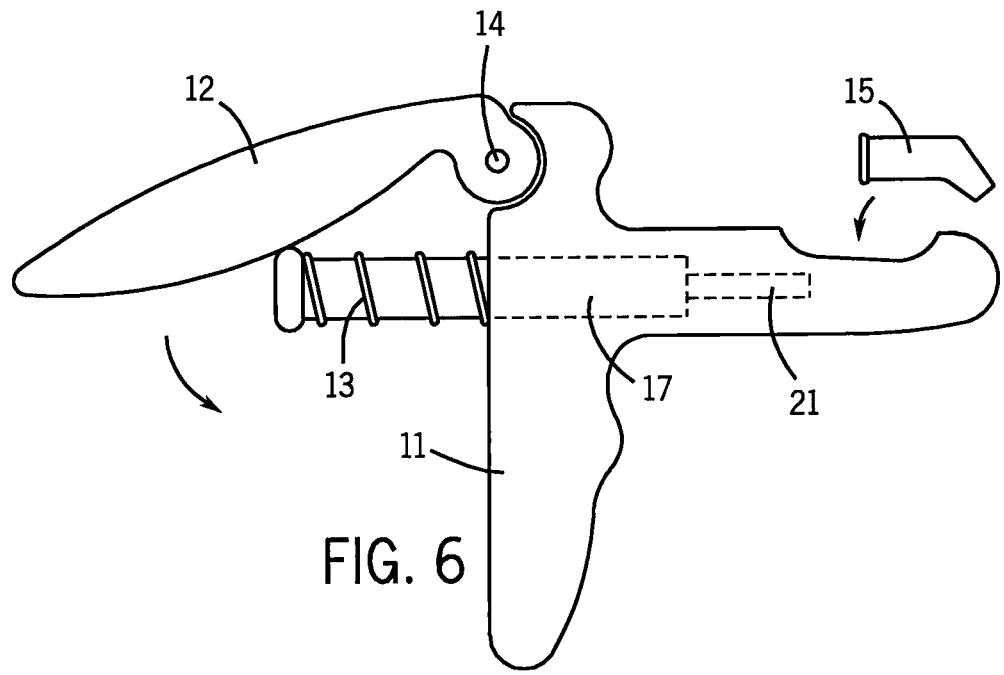
FIG. 6 is a side view of a composite delivery gun and yet to be inserted capsule in which composite resin composite filling material is pre-loaded.
Figure 7:
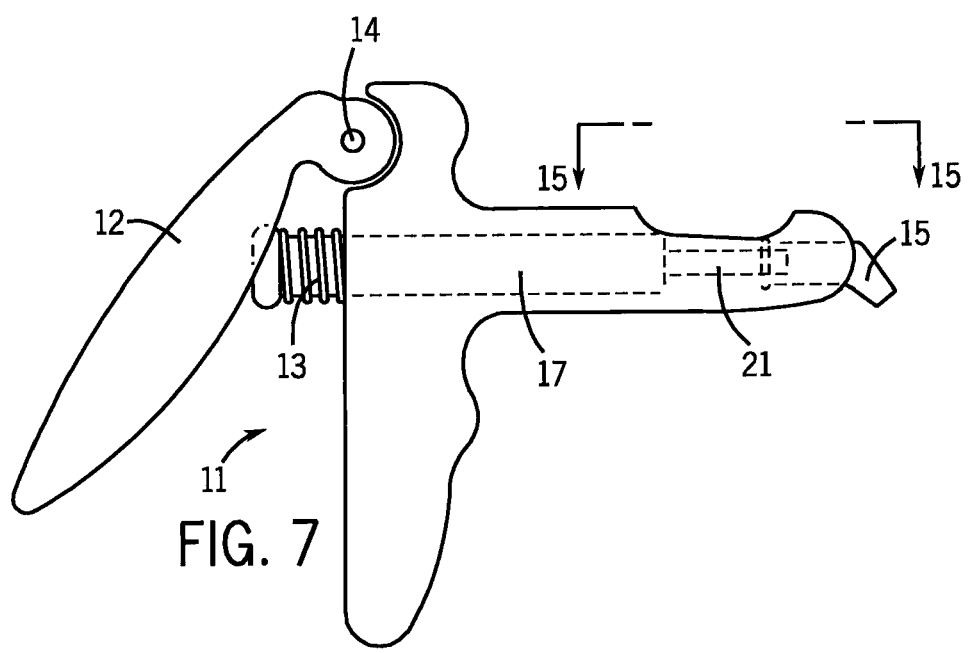
FIG. 7 shows the capsule inserted into the delivery gun of FIG. 6 and ready for expressing into a cavity preparation.
Figure 8:
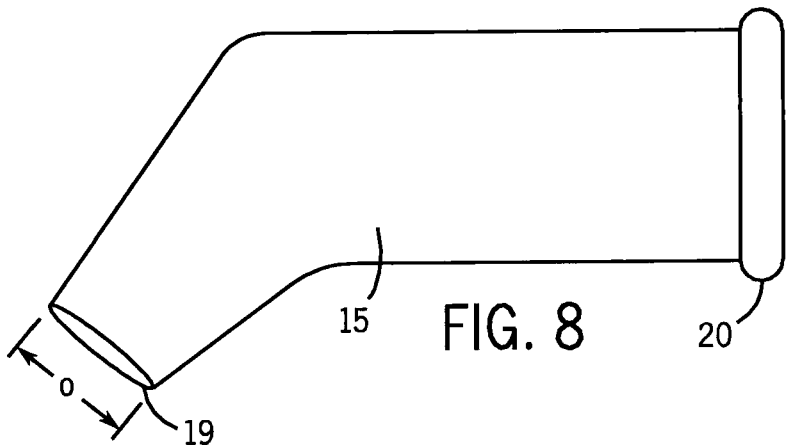
FIG. 8 is an enlarged side view of the capsule of FIG. 6.
Figure 9:
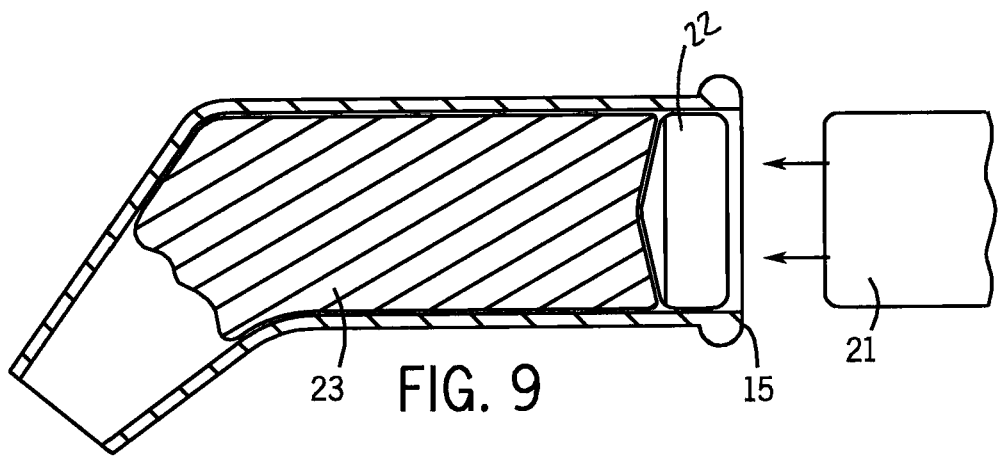
FIG. 9 is a vertical cross-sectional view of the capsule of FIG. 6 showing the position of plunger and the pre-loaded resin composite filling material.
Figure 10:
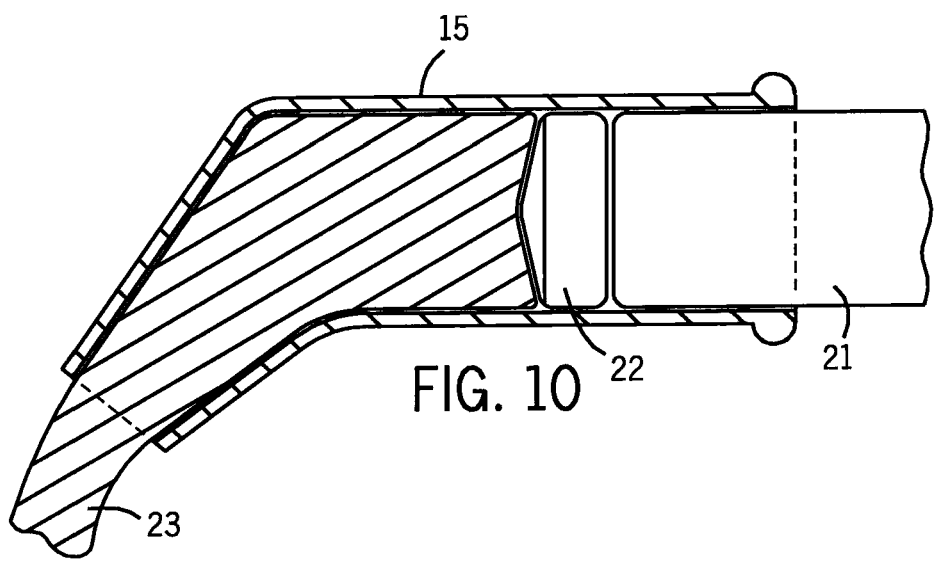
FIG. 10 is a view similar to FIG. 9 showing the extrusion of the resin composite material as the plunger is driven into the barrel of the capsule and pressure is applied to the resin composite.

In FIGS. 6-19, there are shown various dental composite dispensers according to the invention. FIG. 6 shows a side view of a dental composite dispenser gun 11 and a yet to be inserted capsule 15 in which the resin composite filling material is pre-loaded. FIG. 7 shows the capsule 15 inserted into the dispenser gun 11 and ready for expressing into a cavity preparation. The piston 17 drives the rubber plunger 21 which in turn presses the paste composite resin filling material. The handle 12 of the dispenser gun 11 in FIG. 7 has been pressed and is compressing the spring 13. Hinge 14 allows rotation of the handle 12 to press the piston 17. FIG. 8 is a side view, close up of the capsule 15 having a dispensing orifice 19 with inside diameter O (which can be 2.5 mm.) and a rear end 20. FIG. 9 is a cross-sectional view of the capsule 15 showing the position of plunger 21 and the pre-loaded resin composite filling material 23 (shown with cross hatching) which moves forward by way of a rear sliding disc 22. FIG. 10 shows the extrusion of the resin composite material 23 as the plunger 21 is driven into the barrel of the capsule 15 and pressure is applied to the resin composite 23.

FIG. 11 shows a step-down tip 24 according to the invention approximated to the capsule 15 before insertion. The dispensing orifice 25 of the tip 24 is a smaller orifice size O', which diameter can range from approximately 0.75 millimeters to 1.5 millimeters. In FIG. 11, the step down tip 24 is drawn to represent the 1.25 millimeter diameter orifice, which is half the diameter of the size of the dispensing orifice 19 of the example capsule 15 in FIGS. 6-13. FIG. 12 shows the step down tip 24 being inserted in the capsule 15, which can be accomplished with finger pressure or with dental pliers or hemostats or with common needle nose pliers. FIG. 13 shows the step down tip 24 fully inserted into the capsule 15. Note how the annular rib 26 of the tip 24 forms a distended wall section 27 in the capsule 15 that creates the retention needed to retain the step down tip 24.

Figure 14:
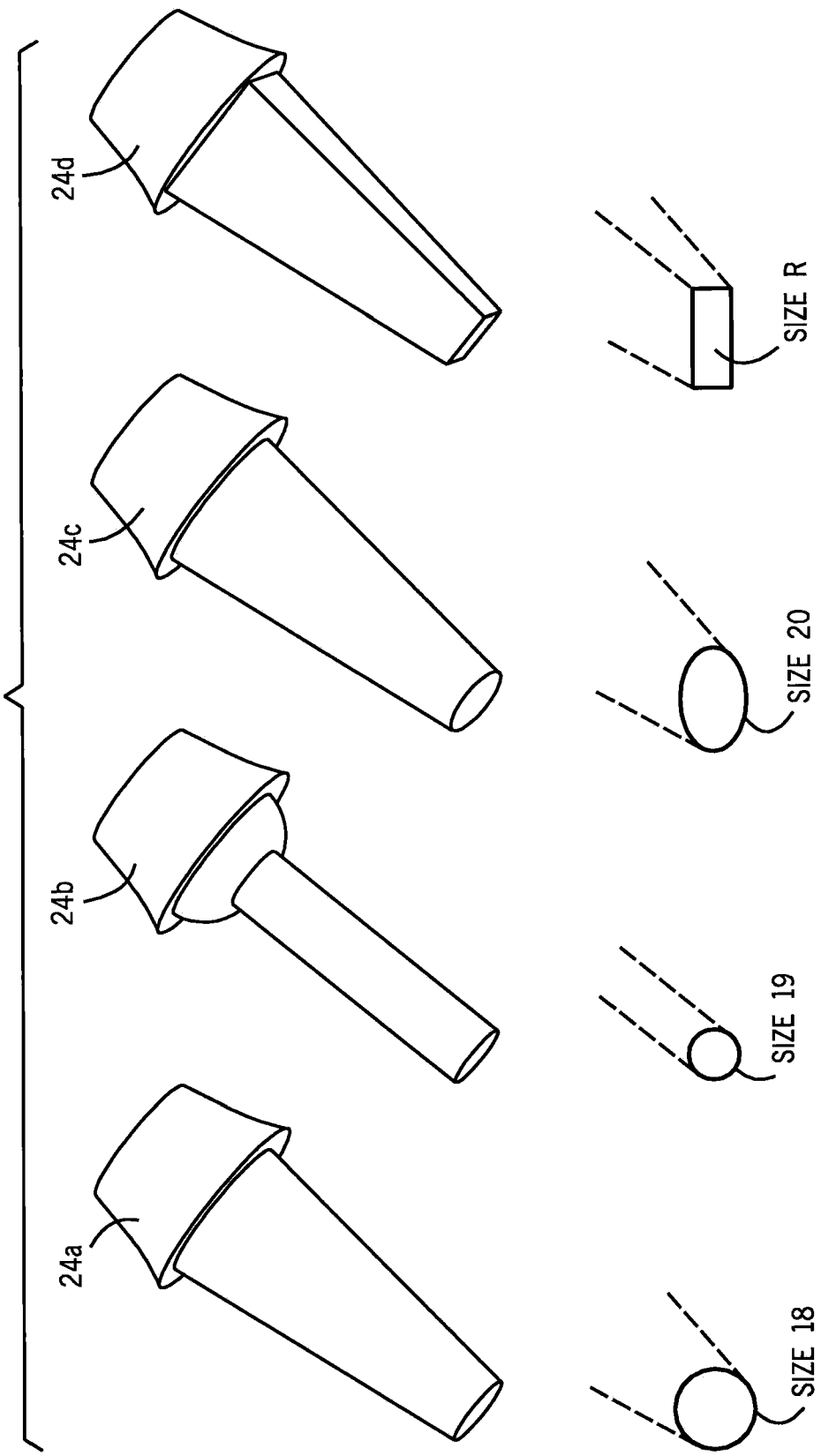
FIG. 14 shows four varieties of the step down tips.

FIG. 14 shows four non-limiting examples of the step down tips. In step down tip 24a, the orifice Size 18 is in the 1 to 1.5 millimeter range for the inside diameter. In step down tip 24b, the orifice Size 19 is for ultraconservative cavities or hard to reach cavities and generally ranges in the 0.75 to 1 millimeter diameter size for the inside diameter. In step down tip 24c, the orifice Size 20 is ovoid (about 1×2 millimeters or 1×3 millimeters inside dimension) for class 11 cavity preparations or other applications where a non round expressed resin composite shape is desired. In step down tip 24d, the orifice size is ribbon shaped R with about 0.5×3 millimeters inside dimension. The ribbon shape is good for restorative fillings as a veneer layer of composite, or a ribbon to line a porcelain onlay or veneer for bonded esthetic porcelain dentistry.

Turning now to FIG. 15, there is shown a dental composite dispenser 11a according to the invention. The dental composite dispenser 11a includes a housing including an end section 30 for dispensing composite. The piston 17 drives the rubber plunger 21 which in turn presses the paste composite resin filling material from the capsule 15 as described above for dispenser 11. The end section 30 has an opening 31 defining a space 33 in which the capsule 15 may be inserted into place as shown in FIG. 15. Resistive heating elements 35 are positioned in the end section 30 adjacent installed capsule 15. The heating elements 35 are in electrical communication with an electrical power supply 37 (batteries in FIG. 15 but AC corded power is also usable). The dispenser 11a includes a switch 38 for supplying electrical power to the heating elements 35 for generating heat adjacent the capsule 15 to heat up the composite material in the capsule 15 before expressing the composite from the hollow step down tip 24e (having an inside diameter in the range of about 0.4 millimeters to about 1.6 millimeters) of the dispenser 11a. Heating the composite allows more highly filled composites (e.g., paste) to be expressed through the step down tips having smaller inside diameters (about 0.4 millimeters to about 1.6 millimeters). In one version of the invention, the capsule 15 is formed from a plastic having higher heat transfer capabilities.

Referring now to FIG. 16, there is shown a dental composite dispenser 11b according to the invention. The dental composite dispenser 11b includes a housing including an end section 30b for dispensing composite. The piston 17 drives the rubber plunger 21 which in turn presses the paste composite resin filling material from the capsule 15 as described above for dispenser 11. The end section 30b has an opening 31b defining a space 33b in which the capsule 15 may be inserted into place as shown in FIG. 16. Resistive heating elements 35a are positioned only at the tip of the end section 30b adjacent the distal end of the installed capsule 15 to create a heating zone 41 at the distal end of the installed capsule 15. The heating elements 35a are in electrical communication with an electrical power supply 37 (batteries in FIG. 16 but AC corded power is also usable). The dispenser 11b includes a switch 38 for supplying electrical power to the heating elements 35a for generating heat adjacent the capsule 15 to heat up the composite material in the capsule 15 before expressing the composite from the hollow step down tip 24e (having an inside diameter in the range of about 0.4 millimeters to about 1.6 millimeters) of the dispenser 11b.

Figure 17:
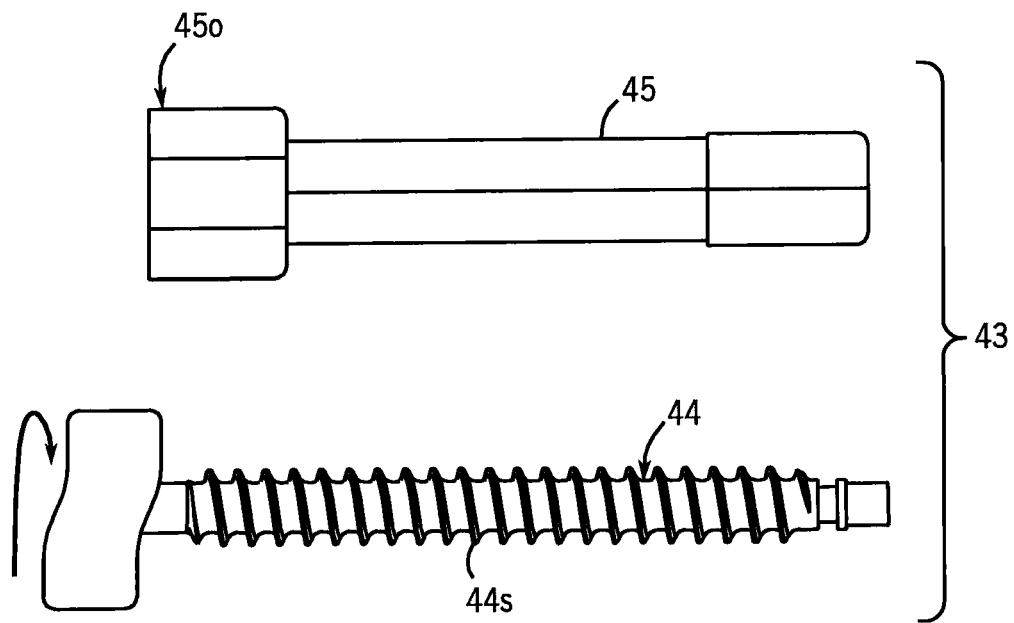
FIG. 17 is a side view of a commercially available syringe for supplying composite resin.

Turning to FIG. 17, there is a side view of a commercially available syringe 43 for supplying composite resin. The syringe 43 includes a plunger 44 having a threads 44s that is threadingly inserted in the open end 45o of hollow barrel 45. By rotating the plunger 44, the plunger 44 advances in the barrel 45 to extrude composite from the tip 46 of the syringe 43.

Referring now to FIG. 18, there is shown a dental composite dispenser 11c according to the invention. The dental composite dispenser 11c includes a housing including an end section 30c for dispensing composite. The end section 30c has an opening 31c defining a space 33c in which the barrel 45 of the syringe 43 of FIG. 17 may be inserted into place as shown in FIG. 18. The piston 17 drives the rubber plunger 21 which in turn presses the paste composite resin filling material from the barrel 45. Resistive heating elements 35b are positioned adjacent barrel 45 to create a heating zone 47. The heating elements 35b are in electrical communication with an electrical power supply 37 (batteries in FIG. 18 but AC corded power is also usable). The dispenser 11c includes a switch 38 for supplying electrical power to the heating elements 35b for generating heat adjacent the barrel 45 to heat up the composite material in the barrel 45 before expressing the composite from the barrel 45 through passage 48 and into hollow step down tip 24f (having an inside diameter in the range of about 0.4 millimeters to about 1.6 millimeters) of the dispenser 11c.

Turning now to FIG. 19, there is shown a dental composite dispenser 11d according to the invention. The dental composite dispenser 11d includes a housing including an end section 30d for dispensing composite. The end section 30d has an opening 31d defining a space 33d. The end section 30d has an a chamber 51 with a fill hole 53 for accepting composite material. After composite is filled into the chamber 51, the piston 17 drives the rubber plunger 21 with plunger head 55 which in turn presses the paste composite resin filling material from the chamber 51. Resistive heating elements 35c are positioned adjacent chamber 51 to create a heating zone 56. The heating elements 35c are in electrical communication with an electrical power supply 37 (batteries in FIG. 19 but AC corded power is also usable). The dispenser 11d includes a switch 38 for supplying electrical power to the heating elements 35c for generating heat adjacent the chamber 51 to heat up the composite material in the chamber 51 before expressing the composite from the chamber 51 through passage 57 and into hollow step down tip 24g (having an inside diameter in the range of about 0.4 millimeters to about 1.6 millimeters) of the dispenser 11d.

Based on the description above of the example dental composite dispensers 11a, 11b, 11c, 11d, it can be appreciated that the dental composite dispensers can include an AC power cord or be cordless (include a battery). The switch 38 of the example dental composite dispensers 11a, 11b, 11c, 11d can include appropriate electrical circuitry such that the heat of the composite can include multiple settings for heat (e.g., 99° F., 130° F., 155° F. or 180° F.) or the heat setting can be variable from 99° F. to 180° F. In FIG. 16, the dispenser 11b can only heat the composite as it exits, therefore not heating the whole capsule 15. The advantage is that the eventual deterioration of the composite from extended and multiple heatings is avoided. With respect to FIGS. 17 and 18, generally a syringe 43 can provide composite to multiple appointments or multiple fillings. A capsule 15 by contrast will only do one or two or three fillings at most. Some fillings require two or more capsules 15 because of the capsule's small size. In FIG. 19, paste composite can be dumped from a tub or a syringe 43 into the chamber 51, then the composite is heated in the chamber 51 and extruded through assorted tips, generally 14 needle gauge up to 20 needle gauge and also non round orifice ribbon shape or ovoid. Because the chamber requires maintenance, it may be preferred to use a disposable chamber that you dump into or a syringe 43 that you load in the dispenser after removing the twisty plunger 44 and use the straight plunger 21 of the dispenser to force composite out of the syringe 43. Of course, a capsule 15 that conforms to the dispenser is also suitable. One can also use a unidose capsule that either has step down tip or the manufacturer of the composite makes preferred orifice sizes. Also, the invention may use a unidose tip from a composite manufacturer with a small orifice (14-20 needle gage—an inside diameter in the range of about 0.4 millimeters to about 1.6 millimeters) that can only be used with heat. This would likely only work if composite is heated.

Figure 20:
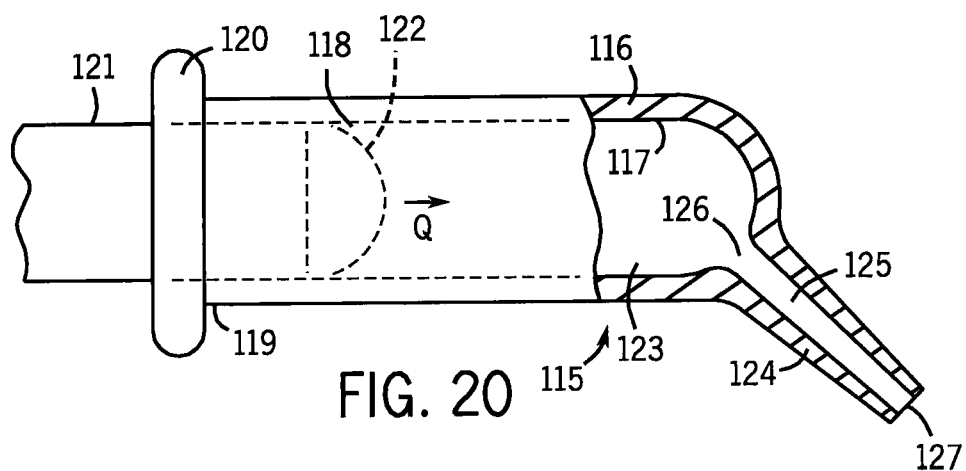
FIG. 20 is a side view, partially in cross-section, of a capsule according to the invention for supplying a dental restorative material to a cavity preparation.

Referring now to FIG. 20, there is shown another capsule 115 for use in a dental composite dispenser according to the invention. The capsule 115 includes a hollow body 116 having an inner surface 117 and a proximal opening 118 at a proximal end 119 of the body 116. An outwardly directed flange 120 is provided at the proximal end 119 of the body 116. A plunger 121 contacts a movable piston 122 that engages the inner surface 117 of the body 116. The piston 122 seals the proximal opening 118 of the body 116. The piston 122 and the inner surface 117 of the body 116 define an interior space 123 of the body 116.

The capsule 115 includes a hollow dispensing orifice 124 having a passageway 125 extending from an inlet 126 to an outlet 127. The inlet 126 is in fluid communication with the interior space 123 of the body 116. A viscous highly filled dental restorative material (not shown) is placed in the interior space 123 of the body 116. Movement of the piston 122 toward the dispensing orifice 124 in direction Q extrudes dental restorative material from the outlet 127 of the dispensing orifice 124. The passageway 125 of the dispensing orifice 124 has an inside diameter in the range of about 0.4 millimeters to about 1.8 millimeters, preferably in the range of about 0.6 millimeters to about 1.6 millimeters, more preferably in the range of about 0.6 millimeters to about 1.2 millimeters, and most preferably in the range of about 0.6 millimeters to about 1.0 millimeters.

The passageway 125 of the dispensing orifice 124 can have other sizes. The passageway 125 can be in the 1 to 1.5 millimeter range for the inside diameter. The passageway 125 can be in the 0.75 to 1 millimeter diameter size for the inside diameter. The passageway 125 can be ovoid (about 1×2 millimeters or 1×3 millimeters inside dimension) for class II cavity preparations or other applications where a non round expressed resin composite shape is desired. The passageway 125 can be about 0.5×3 millimeters inside dimension. The ribbon shape is good for restorative fillings as a veneer layer of composite, or a ribbon to line a porcelain onlay or veneer for bonded esthetic porcelain dentistry.

The piston 122 may connected to the plunger 121 which is part of a syringe-type delivery system. The plunger 121 moves the piston 122 toward the dispensing orifice 124. Alternatively, the capsule 115 may be inserted in a compartment of a dispensing gun (like dispensing gun 11 of FIG. 6). The plunger 121 is part of the dispensing gun (like 21 in FIG. 6). The plunger 121 moves the piston 122 toward the dispensing orifice 124 to extrude dental restorative material from the outlet 127 of the dispensing orifice 124. Optionally, the dispensing gun includes a device for multiplying a force applied to the plunger 121 by a user. This provides extra force extrude the viscous highly filled dental restorative material through the outlet 127 of the dispensing orifice 124. Alternatively, a device for reducing the viscosity of the dental restorative material is provided with the capsule 115. For example, resistive heating elements (such as 35 in FIG. 15) can be positioned in the end section of the dispensing gun adjacent installed capsule 115. The capsules 115 can also be heated in a separate heater before or after installation in the dispensing gun.

The dental restorative material includes a polymerizable (e.g., light curable) resin and a filler. Non-limiting examples of suitable resins include acrylate resins, methacrylate resins, and silorane-based resins. Non-limiting examples of suitable fillers include silica, silicate glass, quartz, barium silicate, strontium silicate, barium borosilicate, strontium borosilicate, borosilicate, lithium silicate, lithium alumina silicate, amorphous silica, calcium phosphate, alumina, zirconia, tin oxide, and titania. The paste composite can include greater than 30% by volume filler, or greater than 40% by volume filler, or greater than 50% by volume filler, or greater than 60% by volume filler, or greater than 70% by volume filler, or greater than 80% by volume filler, or greater than 90% by volume filler. Preferably, the dental restorative material has a volume shrinkage of 3% or less upon curing, More preferably, the dental restorative material has a volume shrinkage of 2% or less upon curing. Most preferably, the dental restorative material has a volume shrinkage of 1% or less upon curing.

Thus, the invention provides methods for the restoration of a decayed portion of an anterior tooth or re-restoration of a previously filled anterior tooth, and also provides dental matrices and composite resin dispensers that may be used in the methods for the restoration of a decayed portion of an anterior tooth.

The invention has many advantages. For example, the step down tips and the heating of the composite allow the dentist to make smaller cavities that would be too small to fill easily with larger tips, especially in light of the fact that most United States dentists are now using magnification (e.g., oculars, operating microscopes and digital video clinical magnification). Also, the step down tips and/or the heating of the composite allow the dentist to more efficiently use an anatomic matrix. An anatomic matrix has more closed off access. Without a smaller orifice on the dispenser tip, it can be difficult to do injection molded composites as the dentist cannot get the large tip of a larger syringe into a conservative cavity that has an anatomic matrix that is "pre-wrapped", impeding the placement of the capsule tip. Without (i) the step down tips and/or (ii) the micro-tip/heated only/paste specific capsules and/or (iii) the composite heater gun with micro-tip paste extrusion tips, a dentist could only squirt the paste on to the tooth or on a pad, then scoop it up on a dental instrument and then try to pack it manually into the cavity preparation. A dental composite dispenser according to the invention heats the composite as the composite is injected into the cavity preparation, that is, the same dispenser heats and injects the composite. Those skilled in the art would recognize further advantages of the invention.

Although the invention has been described in considerable detail with reference to certain embodiments, one skilled in the art will appreciate that the present invention can be practiced by other than the described embodiments, which have been presented for purposes of illustration and not of limitation. Therefore, the scope of the appended claims should not be limited to the description of the embodiments contained herein.

What is claimed is:

1. A method for the restoration of an anterior tooth having an original shape including an interproximal surface, the method comprising:
    (a) removing a portion of the interproximal surface of the tooth to form a hollow cavity preparation;
    (b) surrounding the removed portion of the interproximal surface of the tooth with a matrix, the matrix comprising a non-flat sectional strip having a first end and an opposed second end, wherein the strip includes at least one anatomic feature dimensioned for a surface of an anterior tooth;
    (c) extruding a flowable composite resin into the hollow cavity preparation to create a pool of the flowable composite resin;
    (d) thereafter extruding a paste composite resin filling material into the pool of the flowable composite resin before light curing the pool of the flowable composite resin; and
    (e) simultaneously light curing the flowable composite resin and the paste composite resin filling material contained in the cavity preparation,
    wherein the flowable composite resin has less filler than the paste composite resin filling material.

2. The method of claim 1 wherein:
step (d) comprises extruding the paste composite resin filling material through a step down tip of dispenser.

3. The method of claim 1 wherein:
step (d) comprises extruding the paste composite resin filling material through a step down tip inserted into a capsule containing the paste composite resin filling material, the capsule being loaded in a dispenser.

4. The method of claim 1 wherein:
the paste composite resin filling material has a volume shrinkage of 3% or less upon curing.

5. The method of claim 1 wherein:
the paste composite resin filling material has a volume shrinkage of 1% or less upon curing.

6. The method of claim 1 wherein:
the paste composite filling material includes greater than 30% by volume filler.

7. The method of claim 1 wherein:
the strip has a length from the first end to the second end such that the strip can cover at least 90 degrees around side surfaces of the anterior tooth covered by the strip.

8. The method of claim 1 wherein:
the matrix is tooth and surface specific for the anterior tooth.

9. The method of claim 1 wherein:
the filler is selected from silica, silicate glass, quartz, barium silicate, strontium silicate, barium borosilicate, strontium borosilicate, borosilicate, lithium silicate, lithium alumina silicate, amorphous silica, calcium phosphate, alumina, zirconia, tin oxide, and titania.

* * * * *